United States Patent [19]
Bassi et al.

[11] Patent Number: 5,945,086
[45] Date of Patent: Aug. 31, 1999

[54] GLIADIN-CONTAINING COSMETIC FORMULATIONS

[75] Inventors: Sukh Bassi, Atchison, Kans.; Larry Murphy, Richardson, Tex.; Clodualdo C. Maningat, Platte City; Li Nie, Kansas City, both of Mo.

[73] Assignee: Midwest Grain Products, Atchison, Kans.

[21] Appl. No.: 08/957,435

[22] Filed: Oct. 24, 1997

Related U.S. Application Data

[63] Continuation-in-part of application No. 08/738,094, Oct. 25, 1996, Pat. No. 5,780,013.

[51] Int. Cl.⁶ .................................................. A61K 7/11
[52] U.S. Cl. ...................... 424/45; 424/70.11; 424/59; 424/70.1; 424/70.9; 424/DIG. 1; 424/DIG. 2; 424/47; 424/70.2; 424/78.02; 424/73; 514/2; 514/944; 514/945; 514/937
[58] Field of Search .................................. 424/70.11, 45, 424/59, 73, 70.1, 70.9, DIG. 1, DIG. 2, 47, 70.2, 78.02; 514/2, 944, 945, 937

[56] References Cited

U.S. PATENT DOCUMENTS

| | | | |
|---|---|---|---|
| 4,195,077 | 3/1980 | Marsh et al. | 424/70.11 |
| 4,518,614 | 5/1985 | Parkinson | 424/70.11 |
| 4,897,262 | 1/1990 | Nandagiri et al. | 424/70.11 |
| 5,021,238 | 6/1991 | Martino et al. | 424/DIG. 2 |
| 5,094,838 | 3/1992 | Benson et al. | 424/DIG. 1 |
| 5,126,126 | 6/1992 | Varaprath et al. | 424/47 |
| 5,176,898 | 1/1993 | Goldberg et al. | 424/47 |
| 5,614,173 | 3/1997 | Ulmer et al. | 424/47 |

FOREIGN PATENT DOCUMENTS 1122076  7/1968  United Kingdom .

OTHER PUBLICATIONS

Martino et al., *Spray Technology & Marketing,* Mar. Issue (1992), pp. 34–39.

Johnson, M.A., *Spray Technology & Marketing,* Jun. Issue (1992), pp. 32–40.

*Primary Examiner*—Raj Bawa
*Attorney, Agent, or Firm*—Hovey, Williams, Timmons & Collins

[57] ABSTRACT

Improved aqueous gliadin-containing cosmetic formulations are provided which include form about 0.5–10% by weight gliadin dispersed in an aqueous solvent system together with additional ingredients giving desired end properties. The formulations are preferably selected from the group consisting of hairsprays, hair shampoos and shampoo conditioners, hair styling gels, hair conditioners, instant conditioners, and hair reparatives, as well as sunscreens, shaving creams and bath and shower gels.

7 Claims, No Drawings

GLIADIN-CONTAINING COSMETIC FORMULATIONS

RELATED APPLICATION

This is a continuation-in-part of U.S. application Ser. No. 08/738,094 filed Oct. 25, 1996 now U.S. Pat. No. 5,780,013.

BACKGROUND OF THE INVENTION

1. Field of the Invention

The present invention is broadly concerned with improved cosmetic formulations which contain gliadin as a naturally occurring protein polymer. More particularly, the formulations of the invention are preferably selected from the group consisting of hair care products, e.g., low volatile organic compound (VOC) hairsprays, hair shampoos and shampoo conditioners, hair styling gels, hair conditioners, and hair reparatives, as well as sunscreens, shaving creams and bath and shower gels. The invention pertains to such formulations wherein gliadin is preferably dispersed in an aqueous solvent system with other additional ingredients.

2. Description of the Prior Art

Hairsprays have long been provided as a grooming aid for hairstyling and maintenance purposes. These formulations have been placed in pressurized containers with propellants, or in non-pressurized bottles equipped with simple pump sprayers. Generally, prior hairspray formulations have included significant amounts of synthetic polymers such as polymethylmethacrylate or other acrylic acid-based polymers, vinylmethyl ethers, maleic anhydride or polyvinyl pyrrolidone.

In recent years, environmental concerns have led to the enactment of increasingly stringent VOC standards for hairsprays and other like products. Indeed, the State of California is presently proposing that these products have a maximum VOC content of 55%. At the same time, many consumers have expressed a strong preference for products either devoid of or using only a minimum of synthetic resins; rather, these consumers prefer "all natural" products where possible.

Gliadin is a single-chained protein having an average molecular weight of about 30,000–40,000, with an isoelectric point at pH 4.0–5.0. Gliadin can be obtained by fractionation of wheat gluten and is considered to be a premium product. Gliadin is known to improve the freeze thaw stability of frozen doughs and also improve microwave stability. The product may also be used as a chewing gum base replacer, a pharmaceutical binder, and to improve the texture and mouth feel of pasta products; although gliadin has also been used in certain cosmetic products, it has never found utility in hairsprays or similar compositions.

An enormous variety of other cosmetic products have been produced through the years, for example all manner of lotions, gels, facial masks, sunscreens, shaving creams and hair restoratives. Here again, the consuming public has expressed a desire to purchase and consume products of this character which include "naturally occurring" ingredients insofar as possible.

U.S. Pat. No. 4,518,614 describes a gliadin-containing composition for improving skin texture and moisture, and to diminish wrinkles. The product described in the '614 patent contains gibberellic acid as well as gliadin and lysine. The product contains sufficient acid to give an acid pH, estimated to be no higher than about 4. The '614 patent does not describe any hair product, shaving cream, sunscreen or bath and shower gel.

SUMMARY OF THE INVENTION

The present invention addresses the problems outlined above and provides a variety of cosmetic formulations which include gliadin as an important naturally occurring polymeric component thereof. The cosmetic formulations of the invention are generally aqueous-based with water being the single most predominate ingredient in most of the formulations. Broadly speaking, the cosmetic formulations of the invention comprise from about 0.05–10% by weight gliadin dispersed in an aqueous solvent system, with one or more additional ingredients selected from the group consisting of humectants, emollients, conditioners, thickeners, moisturizing agents, opacifiers, pearl agents, buffering agents, slip agents, feel agents, anti-static agents, acidifiers, preservatives, film formers, plasticizers, setting agents, and suspending agents.

One preferred class of cosmetic formulations in accordance with the invention are low VOC hairspray products. Such formulations comprise from about 0.05–10% by weight gliadin dispersed in aqueous, alcohol-containing solvent system, with the formulation having a pH of from about 3.0–5.5. Such formulations give good hair control without undue discoloration or other undesirable properties. At the same time, the formulations can be prepared with VOC contents on the order of up to about 85%, and more preferably up to about 55%.

In preferred forms, the hairspray formulations include from about 3–7% by weight gliadin and are dispersed within a solvent system making up from about 90–98% by weight of the formulation. The solvent system comprises (and advantageously consisting essentially of) water, alcohol, and acid, such that the water content of the formulation is from about 20–75% by weight (more preferably from about 30–50% by weight) while the alcohol content is from about 20–92% by weight (more preferably from about 30–60% by weight) and the acid is present at a minor level of from about 0.5–3% by weight of the formulation. The presently preferred formulation contains less than 55% by weight alcohol, without alcohol being the only volatile organic compound present; therefore, the VOC content of the formulation is below the most stringent environmental standards now proposed.

The low pH levels of the hairspray formulations are achieved by presence of acid. A variety of acids can be used, with malic acid being the most preferred. Use of this acid insures that the formulation leaves a clearer film on hair.

The remaining types of preferred cosmetic formulations are of aqueous character and contain from about 20–75% by weight water, more preferably from about 30–50% by weight water. The gliadin contents range from about 0.05–10% by weight, more preferably from about 0.2–7% by weight. The additional ingredients in these other cosmetic products are primarily dictated by the type of product in question and the desired end properties. Such additional ingredients are normally selected from the group consisting of humectants, emollients, conditioners, thickeners, moisturizing agents, opacifiers, pearl agents, buffering agents, slip agents, feel agents, anti-static agents, acidifiers, preservatives, film formers, plasticizers, setting agents, and suspending agents. These additional ingredients are typically used in relatively moderate amounts respectively ranging for each individual additional ingredient from about 0.05–10% by weight, and more preferably from about 0.1–8% by weight. The total amount of such additional ingredients in the various formulations ranges from about 4–65% by weight, and more preferably from about 5–60% by weight, and still more preferably from about 15–50% by weight. The specific additional ingredients selected for a particular preparation are matters of choice for the skilled artisan and a number of alternatives exist for each category of additional ingredients.

In the case of hair shampoos and shampoo conditioners, the formulations typically include at least about 6% active detergent therein, and more preferably at least about 8% by weight. These formulations generally have from about 25–75% by weight water, more preferably from about 40–60% by weight water. The pH of the shampoos and shampoo conditioners is normally from about 5–8, more preferably from about 5.5–7.0.

The hair styling gels of the invention contain a large proportion of water, normally from about 65–95% by weight, and more preferably from about 80–90% by weight. The preferred gel-forming polymer system (generally present at a level of at least about 1% by weight, more preferably about 2% by weight) is made up of a polymer including acrylic moieties therein together with a neutralizer such as an amine and most particularly triethanolamine (TEA). The pH of these products ranges from about 5.5–8.5 and more preferably from about 6–7.

The hair conditioners (sometimes referred to as "instant conditioners") have from about 65–95% by weight water, and more preferably from about 70–95% by weight water. The pH of these formulations ranges from about 3–7, and more preferably from about 3.5–4.5. These include at least about 0.3% by weight active cationic hair conditioner.

The hair reparatives hereof preferably include cationic hair conditioners, normally hydrolyzed grain proteins. These materials are present at a level of from about 15–60% by weight, and more preferably from about 25–50% by weight. The water content of the reparatives generally ranges is from about 30–70% by weight, more preferably from about 40–60% by weight. pH levels are from about 3.5–7, and more preferably from about 4–6.5. The reparatives have at least about 2% by weight (active basis of cationic hair conditioner).

The sunscreens of the invention include sunblocking agents, normally metallic oxides, such as titanium dioxide and/or zinc oxide. The sunscreen agents are used at a level of from about 4–20% by weight, more preferably from about 7–15% by weight. The pH of these formulations is from about 4–8, and more preferably from about 5.5–7.2.

The shaving creams are emulsified products of high pH, normally from about 9–14, more preferably from about 11–13. The shaving creams have an active detergent fraction totaling at least about 10% by weight, and more preferably from about 10–15% by weight. The moisture content of these emulsions is quite high, ranging from about 60–95% by weight, and more preferably from about 70–90% by weight.

The bath and shower gels have a relatively high surfactant level of at least about 25% by weight, and more preferably from about 35–70% by weight. The water content ranges from about 25–60% by weight, more preferably from about 30–55% by weight. The pH of these formulations is from about 5.0–8.5, and more preferably from about 6.5–7.5.

DETAILED DESCRIPTION OF THE PREFERRED EMBODIMENTS

The following examples set forth preferred formulations in accordance with the invention. It is to be understood, however, that these examples are provided by way of illustration and nothing therein should be taken as a limitation upon the overall scope of the invention.

EXAMPLE 1

A preferred hairspray formula in accordance with the invention was prepared and contained 53.49% by weight denatured ethanol (95% ethanol SD-40), 3.89% by weight purified gliadin, 41.2% by weight purified water and 1.42% by weight malic acid. The composition was prepared by first sprinkling the gliadin (obtained by the gliadin extraction process described in pending application for U.S. Letters Patent Ser. No. 08/526,078, filed Sep. 11, 1995 and incorporated by reference herein) into the ethanol using a strong impeller agitation until a milky solution was obtained. The water was next slowly added with continued strong agitation. At this point, the pH of the solution was adjusted with the malic acid to a level of about 3.5–3.8. This composition is especially suited for use with a non-pressurized pump spray container. The hairspray formula has a very low VOC content and meets the most stringent of presently proposed environmental standards for such products. At the same time, the formulation completely avoids the use of typical synthetic polymers used in prior hairspray compositions.

While the foregoing formula is presently preferred, a number of variations may be made without departing from the principles of the invention. For example, other solvents can be used in place of at least some of the alcohol, e.g., ethoxydiglycol. The principal issue in the use of such additional solvents is that of maintaining the gliadin in dispersion during extended storage and use. While ethanol is the most preferred alcohol because of its cost and physical properties, other alcohols could be used, most notably isopropanol.

The use of acid in the formulation serves primarily to give a clearer film upon application to hair. While malic acid is preferred, a number of $C_2$–$C_{10}$ mono- or polyhydroxy acids could be employed, such as lactic, tartaric or glycolic acids. The acids would generally be present at levels to achieve a final composition pH of from about 3–5.5 and more preferably from about 3.5–5.0.

Optional ingredients could also be provided in formulations of the invention, e.g., plasticizers, conditioning agents and anti-static agents. The plasticizers would be used to give the hairspray formulation more flexibility as applied to the hair for better hair control. In addition, plasticizers may be used to control flaking or whitening of the composition on the hair. Exemplary plasticizers usable in the context of the invention would include diethyl phthalate, triethylcitrate, and would normally be present at a level of up to about 2% by weight, and more preferably from about 0.01–0.5% by weight.

Conditioning agents would typically be used to increase gloss characteristics on hair. Conditioning agents such as esters (e.g., lactic esters and isopropyl myristate) or polyalkylene glycols (e.g., polyethylene glycols having a molecular weight of from about 180–900) would be suitable for this purpose.

Some aqueous hairspray formulations tend to generate static electric charge in the hair and an appropriate anti-static agent could be added to counteract this effect. Quaternary compounds (e.g., stearalkonium chloride, cetyl pyridinium chloride) could be used for this purpose, typically in minor amounts of up to about 2.5% by weight.

The following table summarizes broad and preferred ranges for the components of hairspray formulations in accordance with the invention.

TABLE 1

| Ingredient | Broad Range % By Weight | Preferred Range % By Weight |
| --- | --- | --- |
| Gliadin | 0.5–10 | 3–7 |
| Total Solvent System[1] | 90–98 | 94–97 |
| Alcohol | 20–92 | 30–60 |
| Water | 20–75 | 30–50 |
| Acid | to pH 3.0–5.5 | to pH 3.5–4.0 |
| Plasticizer(s)* | up to 2% | up to about 0.5% |
| Conditioning Agent(s)* | up to 1% | up to about 0.5% |
| Anti-Static Agent(s)* | up to 0.5% | up to about 0.2% |

[1]Total solvent system comprises water, alcohol, acid and additional non-aqueous solvents, if any.
*Preferred optional ingredients

EXAMPLE 2

A preferred shampoo conditioner was prepared in accordance with the present invention by first combining the Part A ingredients and heating the mixture to 165° F. with agitation. The temperature was maintained at 165° F. and mixing continued for fifteen minutes. The mixture was then cooled to 120° F. The Part B ingredients, except salt, were individually added. The batch was allowed to cool to 90° F. A sufficient quantity of the table salt solution was then added to the final product.

TABLE 2

| Ingredient (property) | % by weight of total composition |
| --- | --- |
| Part A | |
| Sodium lauryl sulfate (@ 28% AI) (foamer, cleanser) | 42.86 |
| Deioinized water | 47.49 |
| Ethylene glycol monostearate (opacifier, pearl agent, thickener) | 2.00 |
| Methylparaben (preservative) | 0.15 |
| Propylparaben (preservative) | 0.05 |
| Standamid KD (cocodiethanolamide) | 3.)) |
| Veluatex (Cocoamidopropyl betaine) (conditioner, thickener) | 3.00 |
| Part B | |
| Gliadin | 1.00 |
| DMDM Hydantoin (preservative) | 0.25 |
| Perfume (Alpine 203–247) | 0.20 |
| Table salt solution (25%) (thickener) | QS |

EXAMPLE 3

A preferred hair styling gel was prepared in accordance with the present invention by first sprinkling the Carbopol 2020 into the quantity of distilled water as set forth under Part A. This Part A mixture was then set aside. The Part B distilled water was then combined with the TEA 50%, slowly sprinkled with gliadin, and mixed until uniform. The Part B mixture was set aside. A Part C mixture was prepared by mixing the Laneto-50 and the perfume together until uniform. Once the Part A mixture and the Part B mixture were uniform, Part B was slowly added with agitation to Part A. Part C was then added and mixed until uniform. DMDM hydantoin was then added to the composition and slowly mixed until uniform.

TABLE 3

| Ingredient (property) | % by weight of total composition |
| --- | --- |
| Part A | |
| Carbopol 2020 (acrylic polymer) (thickener) | 1.00 |
| Deionized water | 50.00 |
| Part B | |
| Deionized water | 38.70 |
| Gliadin (setting agent) | 5.00 |
| Triethanolamine (TEA) 50% (neutralizer for Carbopol 2020) | 4.00 |
| Part C | |
| Laneto-50 (polyethylene glycol 75 lanolin) (plasticizer for gliadin, solubilizer for perfume) | 1.00 |
| Perfume (Olay type #201–132) | 0.10 |
| Part D | |
| DMDM Hydantoin (preservative) | 0.20 |

EXAMPLE 4

A preferred sunscreen was prepared using the ingredients of Table 4. First, the Part A ingredients were combined and mixed using a high shear mixer. The Parts C ingredients were then mixed until uniform, and the Part B ingredient was added with high shear mixing until the pigments were thoroughly dispersed and uniform. The mixture of Parts B and C ingredients, and Part A ingredients, were separately heated. to 160° F. The Parts B and C ingredients were then mixed with the Part A ingredients using high shear mixing. This combined mixture was then cooled to 120° F., and the Part D ingredient was added with mixing until uniform. The entire mixture was then cooled to 90° F.

TABLE 4

| Ingredient (property) | % by weight of total composition |
| --- | --- |
| Part A | |
| Methylparaben (preservative) | 0.15 |
| Deionized water | 53.10 |
| Gliadin (suspending agent, film former) | 2.00 |
| Part B | |
| Titanium dioxide and zinc oxide (Cardre 79790 dispersion, 22% TiO$_2$, 14% ZnO) (sunscreen agent) | 30.00 |
| Part C | |
| Propylparaben (preservative) | 0.05 |
| Trivent OC-G (capryl triglyceride) (emollient) | 8.00 |
| Trivasol BW (polyethylene glycol 8 capryl triglyceride) (emulsifier) | 5.00 |
| Part D | |
| Germal II (diazolidinyl urea) (preservative) | 0.20 |
| Hec 250 HR (hydroxyethyl cellulose) (thickener) | 1.50 |

EXAMPLE 5

A preferred instant conditioner is prepared in accordance with the present invention by combining all of the Part A ingredients in a tank equipped with sweep agitation and heating the composition to 170° F. The composition should be mixed well in order to avoid local overheating and to dissolve the powdered protein. At 170° F., continue mixing until the product is smooth and uniform. Cool the composition to 120° F., continue agitating, and add the perfume. Adjust the pH to 3.4–3.8 with the lactic acid solution. Thicken with salt solution as needed.

TABLE 5

| Ingredient (property) | % by weight of total composition |
| --- | --- |
| Part A | |
| Deionized water | 82.90 |
| Aqua Pro TM II QWS (steardi-ammonium hydrolyzed wheat protein) (cationic hair conditioner) | 8.35 |
| Glycerol monostearate SE (Lipomulse 165) (glycerol monostearate + polyethylene glycol 100 stearate) (emulsifier) | 3.00 |
| Cetyl alcohol (thickener, opacifier) | 3.50 |
| Aqua Pro TM II WG Gliadin (conditioner and hair repair agent) | 0.20 |
| Methylparaben (preservative) | 0.15 |
| Part B | |
| Lactic acid (44%) (acidifier) | 0.80 |
| Perfume (Alpine 137–326) | 0.15 |
| Salt solution (25%) (thickener) | QS |

EXAMPLE 6

A preferred aerosol shaving cream is prepared in accordance with the present invention by combining the water, stearic acid, glycerine, and corn oil fatty acids and heating the mixture to 175° F. Sprinkle Aqua Pro TM II WG into the mixture and agitate. With strong agitation, add the sodium hydroxide and potassium hydroxide solutions. Continue agitating and add lauric/myristic diethanolamine. Continue agitating and add the coconut oil. Cool the mixture to 120° F. and then add the perfume. Cool to 95° F. The product is pressurized with ±2.8% of a hydrocarbon blend consisting of isobutane/propane in a ratio of 87 parts to 13 parts, respectively.

TABLE 6

| Ingredient (property) | % by weight of total composition |
| --- | --- |
| Stearic acid (double pressed) (soap former) | 7.16 |
| Glycerine (slip agent, moisturizer) | 2.71 |
| Lauric/myristic diethanolamide | 1.00 |
| Corn oil fatty acids (soap former) | 1.00 |
| Sodium hydroxide (20%) (neutralizer for fatty acids) | 1.20 |
| Potassium hydroxide (34.2%) (neutralizer for fatty acids) | 3.42 |
| Coconut oil (soap former) | 0.25 |
| Perfume | 0.50 |
| Aqua Pro TM II WG (MWGP) (Gliadin) (slip agent) | 0.40 |
| Deioinized water | 82.36 |

EXAMPLE 7

A preferred bath and shower gel is prepared in accordance with the present invention by combining sodium laureth sulfate, water, cocamide DEA, PEG 150 distearate, pationic ISL, methylparaben, and propyl paraben in a mixing kettle equipped with sweep agitation. Begin mixing and heat the composition to 165° F. Mixing should continue until the composition is completely clear and all of the parabens have been dissolved. Maintain the temperature of the composition at 165° F.

Slowly add the gliadin to the composition and mix until uniform. With agitation, sprinkle ethylene glycol distearate into the composition. The flakes will melt and the product will become opaque. Mix for at least thirty minutes until all flakes dissolve and the product is uniform. Cool the product to 120° F. and add the DMDM hydantoin. Mix for approximately ten minutes until the product is uniform. Cool to 90° F., add perfume, mix until uniform and transfer to storage.

TABLE 7

| Ingredient (property) | % by weight of total composition |
| --- | --- |
| Sodium lauryl sulfate (2 mole) (foamer, cleanser) | 50.00 |
| Deionized water | 39.90 |
| Cocamide diethanolamine (DEA) (thickener, foam stabilizer) | 4.00 |
| Ethylene glycol monostearate (opacifier) | 2.00 |
| Polyethylene glycol (PEG) 150 distearate (thickener) | 0.50 |
| Pationic ISL (RITA) (sodium isostearoyl lactylate) (thickener, feel agent) | 2.00 |
| Methylparaben (preservative) | 0.15 |
| Propylparaben (preservative) | 0.05 |
| Gliadin (feel agent) | 1.00 |
| DMDM Hydantoin (preservative) | 0.20 |
| Perfume (Alpine 203–247) | 0.20 |

EXAMPLE 8

A preferred hair reparative is prepared in accordance with the present invention by adding the Salcare SC 96 to the deionized water and mixing until uniform. Next, add the Germal II, Aqua Pro II WP, Aqua Pro QWs and Aqua Pro II WAA to the mixture with agitation. Sprinkle the gliadin into the mixture and continue agitation until uniform. Separately combine the polysorbate 20 and the perfume. Add this combination to the mixture and agitate for fifteen minutes. Adjust the pH to 4.0 with the lactic acid solution.

TABLE 8

| Ingredient (property) | % by weight of total composition |
| --- | --- |
| Aqua Pro II WP (hydrolyzed wheat protein) (hair repairer) | 40.00 |
| Aqua Pro QWS (steardiammonium, hydrolyzed wheat protein) (cationic anti-static conditioner) | 3.00 |
| Aqua Pro II WAA (wheat amino acids) (hair repair agent, moisturizer) | 1.00 |
| Gliadin (hair repairer and moisturizer) | 2.00 |
| Deionized water | 51.50 |
| Salcare SC-96 (acrylic polymer) (thickener) | 5.00 |
| Polysorbate 20 (perfume stabilizer) | 1.00 |
| Perfume (Fresh Blossoms #201–130) | 0.20 |
| Germal II (diazolidinyl urea) | 0.90 |
| Lactic Acid (acidifier) | QS | we claim:

1. An aqueous cosmetic formulation selected from the group consisting of hair shampoos and shampoo conditioners, hair styling gels, hair conditioners, hair reparatives, sunscreens, shaving creams, and bath and shower gels and comprising an amount of gliadin dispersed in an aqueous solvent system, in combination with at least one additional ingredient selected from the group consisting of humectants, emollients, conditioners, thickeners, moisturizing agents, opacifiers, pearl agents, buffering agents, slip agents, feel agents, anti-static agents, acidifiers, preservatives, film formers, plasticizers, setting agents, and suspending agents, said formulation including from about 0.05–10% by weight gliadin, from about 20–75% by weight water and from about 0.05–10% by weight of each of said additional ingredient(s) employed, wherein:

(a) said hair shampoos and shampoo conditioners further comprising at least about 6% detergent;

(b) said hair styling gels further comprising a gel-forming polymer system;

(c) said hair conditioners further comprising at least about 0.3% by weight cationic hair conditioner;

(d) said hair reparatives further comprising at least about 2% by weight cationic hair conditioner;

(e) said sunscreens further comprising a sunblocking agent;

(f) said shaving creams further comprising at least about 10% by weight detergent and having a basic pH; and (g) said bath and shower gels further comprising at least about 25% by weight surfactant.

2. The formulation of claim 1, said gliadin being present at a level of from about 0.2–7% by weight.

3. The formulation of claim 1, said formulation having an acidic pH.

4. The formulation of claim 1, said formulation including a plurality of said additional ingredients.

5. The formulation of claim 4, said plurality of additional ingredients being present at a total level of from about 4–65% by weight.

6. The formulation of claim 5, said level being from about 5–60% by weight.

7. The formulation of claim 1, each of said additional ingredient(s) employed being present at a level of from about 0.1–8% by weight.

* * * * *